(12) United States Patent
Tan (10) Patent No.: US 9,945,768 B2
(45) Date of Patent: Apr. 17, 2018

(54) METHOD AND APPARATUS FOR A PORTABLE PM2.5 MONITORING DEVICE

(71) Applicant: Zhongchao Tan, Waterloo (CA)

(72) Inventor: Zhongchao Tan, Waterloo (CA)

( * ) Notice: Subject to any disclaimer, the term of this patent is extended or adjusted under 35 U.S.C. 154(b) by 169 days.

(21) Appl. No.: 14/896,400

(22) PCT Filed: Jun. 5, 2014

(86) PCT No.: PCT/CA2014/050517
§ 371 (c)(1),
(2) Date: Dec. 7, 2015

(87) PCT Pub. No.: WO2014/194424
PCT Pub. Date: Dec. 11, 2014

(65) Prior Publication Data
US 2016/0116390 A1    Apr. 28, 2016

Related U.S. Application Data

(60) Provisional application No. 61/956,284, filed on Jun. 5, 2013.

(51) Int. Cl.
*G01N 15/02* (2006.01)
*G01N 1/22* (2006.01)
*G01N 15/00* (2006.01)

(52) U.S. Cl.
CPC ....... *G01N 15/0255* (2013.01); *G01N 1/2211* (2013.01); *G01N 2001/2276* (2013.01); *G01N 2015/0046* (2013.01); *G01N 2015/0277* (2013.01); *G01N 2015/0288* (2013.01)

(58) Field of Classification Search
CPC ............ G01N 15/0255; G01N 1/2211; G01N 2001/2276; G01N 2015/0277; G01N 2015/0288
See application file for complete search history.

(56) References Cited

U.S. PATENT DOCUMENTS

| 4,301,002 A | 11/1981 | Loo |
| 4,767,524 A * | 8/1988 | Yeh .......................... B07B 7/00 209/133 |
| 8,012,231 B2 | 9/2011 | Saitoh et al. |
| 8,243,274 B2 | 8/2012 | Aiken et al. |

(Continued)

*Primary Examiner* — Hezron E Williams
*Assistant Examiner* — David Z Huang (57) ABSTRACT

The disclosure is directed at apparatus for portable PM2.5 monitoring including a PM2.5 sampling device including a housing portion for collecting and separating air-borne particulate matter, an inlet port, connected to the housing portion, for receiving the air-borne particulate matter, a core portion, located within the housing portion, the core portion assisting in generating a cyclonic airflow pattern to produce a uniflow system for separating particulate matter below a predetermined size from particulate matter above a predetermined size within the air-borne particulate matter, and an outlet port for receiving the particulate matter below the predetermined size; a particle counter, connected to the outlet port, for receiving the particulate matter smaller than the predetermined size and for determining a mass of the particulate matter below the predetermined size; and a processor for determining a PM2.5 level based on the mass of the particulate matter below the predetermined size.

22 Claims, 6 Drawing Sheets

(56) References Cited

U.S. PATENT DOCUMENTS

2002/0122177 A1* 9/2002 Sioutas ............... G01G 17/04
356/336
2011/0011158 A1* 1/2011 Bodily ............... G01N 1/2211
73/23.41

* cited by examiner

METHOD AND APPARATUS FOR A PORTABLE PM2.5 MONITORING DEVICE

CROSS-REFERENCE TO RELATED APPLICATIONS

This application claims the benefit of priority of U.S. Provisional Patent Application No. 61/956,284 filed Jun. 5, 2013, which is hereby incorporated by reference.

FIELD OF THE DISCLOSURE

The disclosure is generally directed to monitoring devices and more specifically at a method and apparatus for a portable PM2.5 monitoring device.

BACKGROUND OF THE DISCLOSURE

Over the past number of years, there has been a growing interest in monitoring air quality to improve the health of society. By monitoring the air quality, determinations can be made with respect to the amount of particulate matter, both larger and smaller, which is floating in the air and which may be breathed in by individuals. In some countries, government regulations concerning ambient air quality have evolved towards monitoring and regulating smaller particles known as PM2.5.

Therefore, in order to monitor the air quality, air quality monitoring devices have been created and are continuously being improved. These devices may be used for research purposes to study the characteristics of particulate air pollution to see if the characteristics meet with acceptable levels of particulate air pollution with respect to human health or government regulations.

While various devices are known, these devices tend to be large scale monitoring devices which are permanently stationed in different locations.

Therefore, there is provided a novel method and apparatus for a portable PM2.5 monitoring device.

SUMMARY OF THE DISCLOSURE

In one aspect of the disclosure, there is provided an apparatus for PM2.5 sampling including an inlet port for receiving air-borne particulate matter; apparatus for creating a cyclonic airflow pattern within the system to produce a uniflow system to separate larger pieces of particulate matter from smaller pieces of particulate matter; an outlet port for receiving the smaller pieces of particulate matter; wherein the received smaller pieces of particulate matter are transmitted for further counting.

In another aspect, there is provided an apparatus for PM2.5 sampling including a housing portion for collecting and separating air-borne particulate matter; at least one inlet port, connected to the housing portion, for receiving the air-borne particulate matter; a core portion, located within the housing portion, the core portion assisting in generating a cyclonic airflow pattern to produce a uniflow system for separating particulate matter below a predetermined size from particulate matter above a predetermined size within the air-borne particulate matter; and an outlet port for receiving the particulate matter below the predetermined size.

In yet a further aspect, there is provided apparatus for portable PM2.5 monitoring including a PM2.5 sampling device including a housing portion for collecting and separating air-borne particulate matter, an inlet port, connected to the housing portion, for receiving the air-borne particulate matter, a core portion, located within the housing portion, the core portion assisting in generating a cyclonic airflow pattern to produce a uniflow system for separating particulate matter below a predetermined size from particulate matter above a predetermined size within the air-borne particulate matter, and an outlet port for receiving the particulate matter below the predetermined size; a particle counter, connected to the outlet port, for receiving the particulate matter smaller than the predetermined size and for determining a mass of the particulate matter below the predetermined size; and a processor for determining a PM2.5 level based on the mass of the particulate matter below the predetermined size.

DESCRIPTION OF THE DRAWINGS

Embodiments of the present disclosure will now be described, by way of example only, with reference to the attached Figures.

DETAILED DESCRIPTION OF THE DISCLOSURE

The disclosure is directed at a method and apparatus for monitoring air quality. The portable apparatus includes a PM2.5 sampler which, in the preferred embodiment, is a uniflow cyclone or uniflow cyclone device. This means that the air being tested and the particulate matter being monitored enter and exit the PM2.5 sampler in the same direction.

Figure 1:
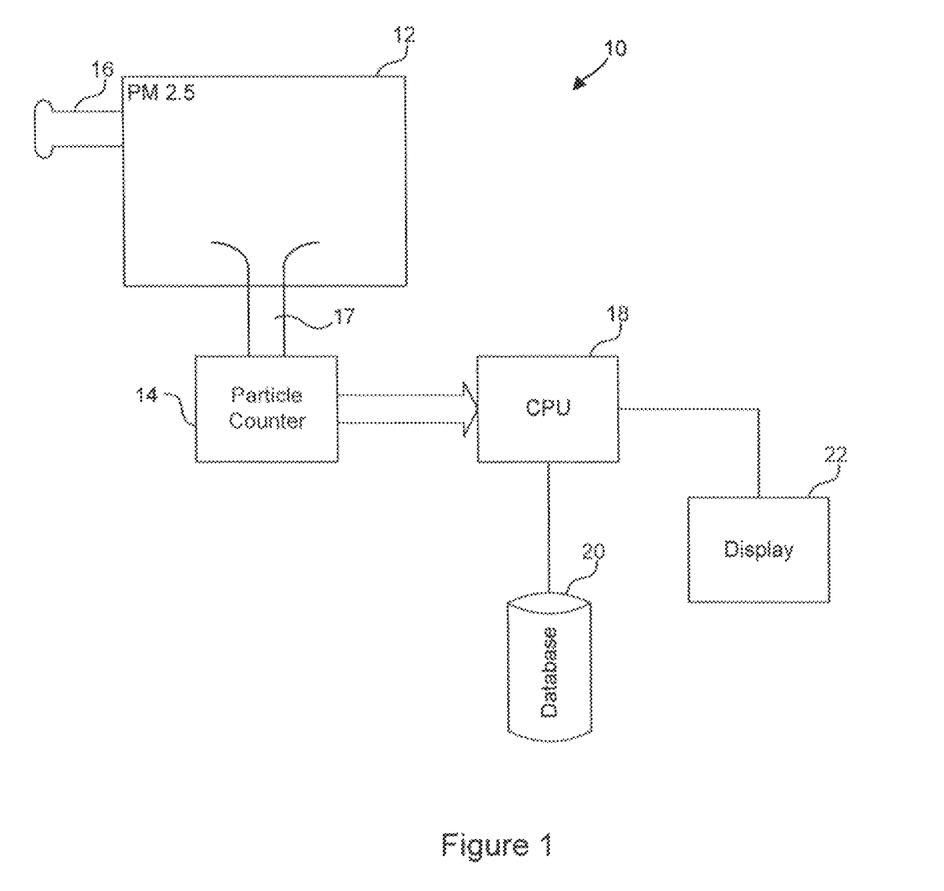
FIG. 1 is a schematic diagram of an apparatus for air quality monitoring.

Turning to FIG. 1, a schematic diagram of a portable apparatus for PM2.5 measurement is shown. The monitoring may be performed in real-time. The system 10 includes a PM2.5 sampler 12 which is connected to a particle counter 14. The PM2.5 sampler 12 receives particulate matter, or air-borne particulate matter, from the atmosphere through an inlet port 16 and then separates pieces of particulate matter which are larger than a predetermined size, or larger particulate matter, from pieces of particulate matter which are less than the predetermined size, or smaller particulate matter. For instance, as the sampler 12 is a PM2.5 sampler, the predetermined size is 2.5 μm which is a standard index regulated by the World Health Organization (WHO). Particulate matter which is less than 2.5 μm (in diameter) may also be described as fine particles. The separation of the particulate matter will be described in more detail with respect to FIG. 2. After separation, the smaller particulate matter exits the PM2.5 sampler via an outlet port 17 and is directed to the particle counter 14. In one embodiment, the particle counter includes a pump which sucks the smaller particulate matter from the PM2.5 sampler 12 through the outlet port 17. The pump may also provide adequate suction to draw the air-borne particulate matter into the PM2.5 sampler as well to assist in producing airflow patterns to separate the particulate matter. The particle counter 14 receives the collected smaller particulate matter and counts the number of particles within the smaller particulate matter. In another embodiment, the particle counter measures and tallies the number of individual particles and their sizes within the smaller particulate matter and then translates the size and numbers into a representative digital signal. The particle counter 14 may also determine or calculate other characteristics of the collected smaller particulate matter.

A particle counter is an instrument that is capable of counting particles entering into the particle counter. Particle counters can either use light scattering, light obscuration, electrical techniques or direct imaging techniques for the counting process. In general, particle counters which are currently available are not specifically designed for measuring the mass of particulate matter, or more specifically, the mass of the smaller particulate matter and only count the number of all particles passing through the counter regardless of their sizes. However, these particle counters may still be used to assist in determining the mass of the smaller particulate matter.

As shown, the particle counter 14 is connected to, and in communication with, a central processing unit (CPU) 18 to transmit the count or the representative digital signal, possibly along with the other data representing characteristics of the smaller particulate matter, so that this data or information may be processed by the CPU 18. The system 10 may further include a database 20 for storing the count or the representative digital signal, the other data or any measurements or calculations resulting from the processing of the data from the particle counter 14. After processing the data, the CPU 18 may display the results on a monitor or display 22 to a user. This information may be, but not limited to, the PM2.5 level (preferably in the unit of μg/m$^3$) in the air surrounding the system.

With high resolution particle counters, mass concentration can be calculated by the relationship between the number of particulate matter and its calculated volume. In a preferred embodiment, the data is processed by a particle counter CPU (or by CPU 18) such that mass concentration vs. particle diameter can be determined.

Alternatively, a user can calculate the mass of the smaller particulate matter with the assumption that all of the individual pieces of particulate matter are spherical with an assumed density based on a pre-calibrated or pre-stored value. In one embodiment, the following equation may be used:

$$M = \rho\left[n_1 \frac{1}{6}\pi d_{m1}^3 + n_2 \frac{1}{6}\pi d_{m2}^3 + \ldots + n_n \frac{1}{6}\pi d_{mn}^3\right] = \frac{1}{6}\pi\rho[n_1 d_{m1}^3 + n_2 d_{m2}^3 + \ldots + n_n d_{mn}^3] = \frac{1}{6}\pi\rho\Sigma n_i d_{m(i)}^3$$

In another embodiment, if a low resolution particle counter 14 is being used, the total amount of smaller particulate matter is counted and separated into different size ranges, or counting channels. For instance, the size ranges, or counting channels, may be defined as <1 μm, between 1 μm and 2 μm, between 2 μm and 2.5 μm and greater than 2.5 μ. The particle counter then detects determines the number of particles for each range or channel. Other channel distributions may also be used. By connecting the PM2.5 sampler 12 in front of this type of portable particle counter 14, a data processing algorithm may be used to compensate the inaccuracy caused by channel width. This is discussed in more detail below.

In operation, the CPU 18 may use different methods for processing the data that is received from the particle counter 14. In one method, the mass of all the particles which exit the sampler 12 through the outlet port shall be considered as the mass of the particulate matter smaller than predetermined size, say the particulate matter which is less than 2.5 μm, that is, PM2.5. In order to obtain the information to be displayed, a data processing algorithm is used in order to deduce PM2.5 from the count of particles exiting the PM2.5 sampler. There are at least two ways to calculate the mass of particles exiting the PM2.5 sampler: 1) add up the mass of the smaller particulate matter which is collected or 2) log-normal distribution based mass derived from counter distribution.

In the summation of the mass collected embodiment, The number of particles which enter the particle counter for either distribution range or channel is determined, along with the total number of particles (the count) such that their total mass may be calculated with the following equation:

$$M = \frac{1}{6}\pi\rho[n_1 d_{m1}^3 + n_2 d_{m2}^3 + \ldots + n_n d_{mn}^3] = \frac{1}{6}\pi\rho\sum n_i d_{m(i)}^3$$

Particle mass concentration is obtained using both the mass calculation result and air volume measurement which can be obtained from a flow meter (preferably located within the particle counter). In this calculation, $n_i$ is the normalized result regardless of the selected ranges within the channels. The mean diameter of a channel range i $d_{m(i)}n_i$ is known from particle counting parameters setting, which is calculated using $$d_{m(i)} = \frac{1}{2}[d_{p(i)} + d_{p(i+1)}]$$

The mass of all particles penetrating through the PM2.5 sampler in the bulk air can now be determined.

In the log-normal based distribution calculation embodiment, it is understood that total particulate matter follows a log-normal distribution which enables parallel straight lines representing particle counter, surface and volume in a log-probability chart. However, it is not clear whether the particles exiting the PM2.5 sampler still has a log-normal distribution such that it is to be experimentally confirmed, however this may be confirmed through experiments as performed by the inventors.

If the particle distribution is still log-normal then it can be applied to a particle number or count, surface and mass. Understanding the log-probability chart and the related calculation process, based on the fact that particle diameters obey log-normal distribution, one can produce a straight line in a log-probability chart. The count mean diameter (CMD) and standard deviation (σ) can be determined from the log-probability chart. Therefore, the mass of all the particles exiting the PM2.5 sampler may be determined using:

$$PM_{2.5} = \frac{1}{6}N\pi(d_{\bar{m}})^3$$

where $$d_{\dot{m}}=CMD\ e^{[1.5(ln\sigma)^2]}$$

After determining the mass, this information is then transmitted to the CPU for processing and display or this determination may be performed by the CPU.

Figure 2A:
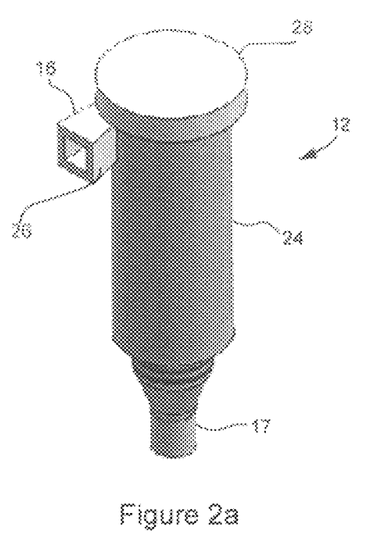
FIG. 2*a* is a perspective view of a PM2.5 sampler.
Figure 2B:
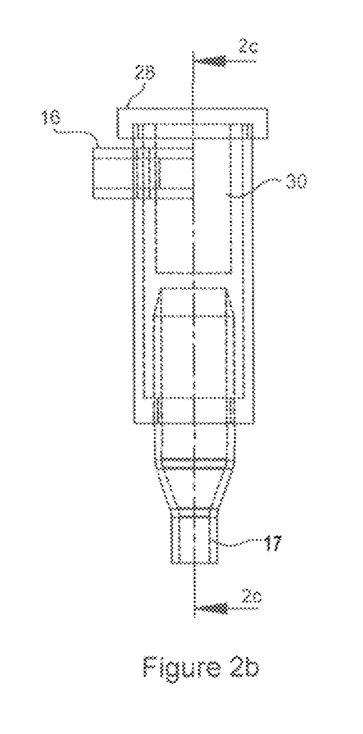
FIG. 2*b* is a side view of the PM2.5 sampler with the internal components in dotted lines.
Figure 2C:
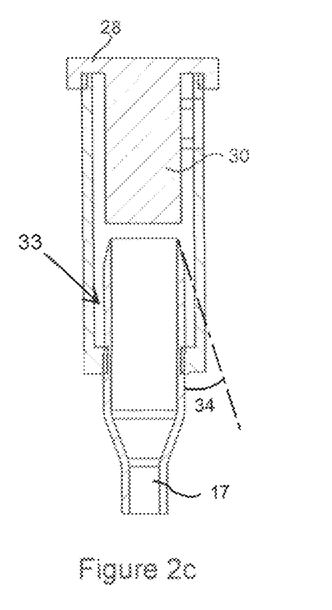
FIG. 2*c* is a cut-away view taking along line 2*c*-2*c* of FIG. 2*b*.

Turning to FIG. 2a, a perspective view of a PM2.5 sampler for use in the apparatus of FIG. 1 is shown, FIG. 2b is side view of the PM2.5 sampler with a transparent housing and internal components shown in dotted lines while FIG. 2c is a cut-away view taken along line 2c-2c of FIG. 2b.

Figure 5:
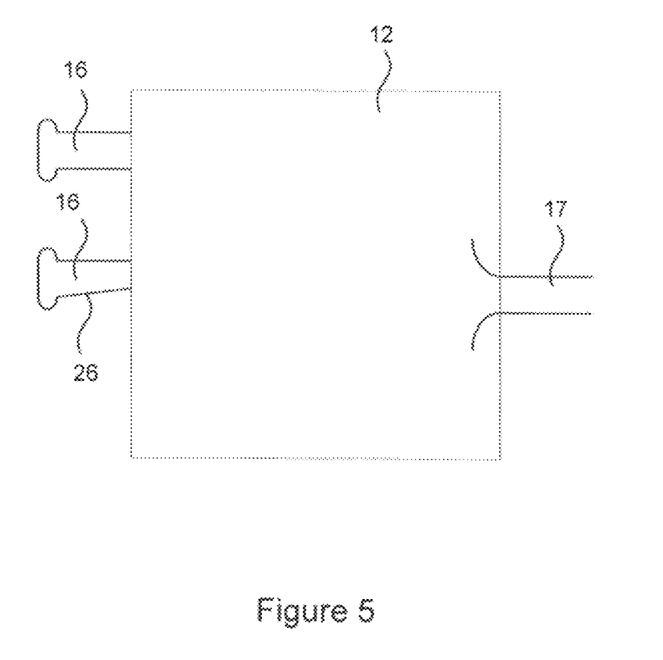
FIG. 5 is a schematic diagram of another embodiment of a PM2.5 sampler.

While larger cyclone type sampling devices are known, the portable, or mini-cyclone, disclosed herein provides advantages over these larger devices. Firstly, the mini-cyclone device allows the PM2.5 sampler or the sensing device to be portable rather than being a permanent fixture and only being able to monitor air quality at one specified location. Other advantages include, but are not limited to, the ability to install or integrate the sampler upstream from the particle counter 14, the sampler 12 may include multiple inlet ports (as shown in FIG. 5), the inlet ports may be manufactured to include an angle of less than about 15 degrees to minimize particle loss during the sampling process and the total flow rate of the air sampled shall allow for a cut size of 2.5 μm to improve smaller particulate matter collection or separation. As would be understood, other angles such as less than 30 degrees may also be used for the inlet ports.

The PM2.5 sampler 12 includes a housing portion 24 with the input port 16. In the current embodiment, the input port 16 has a square cross-section opening although other cross-sections are contemplated. The inlet port 16 includes an angled wall 26 (also shown in FIG. 5). The input port 16 may receive particulate matter directly from the atmosphere or a hose (not shown) may be connected directly to the input port 16 to fill the sampler 12 with the particulate matter. In one embodiment, the particulate matter is drawn into the sampler via a pump providing a suction pressure either from within the sampler or the particle counter (after being attached to the sampler).

At a bottom portion of the housing portion 24 is an outlet port 17 through which collected smaller particulate matter may be transmitted to the particle counter (as shown in the apparatus of FIG. 1). The inlet port 16 and the outlet port 17 are located at opposing ends of the housing portion 24 so that the air flow is unidirectional whereby the air and the particulate matter flow in the same direction. The housing portion 24 can further include a cover portion 28 which can either be snapped on or be threaded on to the housing portion 24.

Each of the inner surfaces of the PM2.5 sampler are manufactured with conductive material to avoid particle loss due to its deposit on the surfaces within the sampler caused by electrostatic interaction. In other words, the inner surface of the housing portion 24, the inner surface of the inlet port 16 and the inner surface of the outlet port 17 are all made of a conductive material such as a metal or a conductive plastic.

Figure 2D:
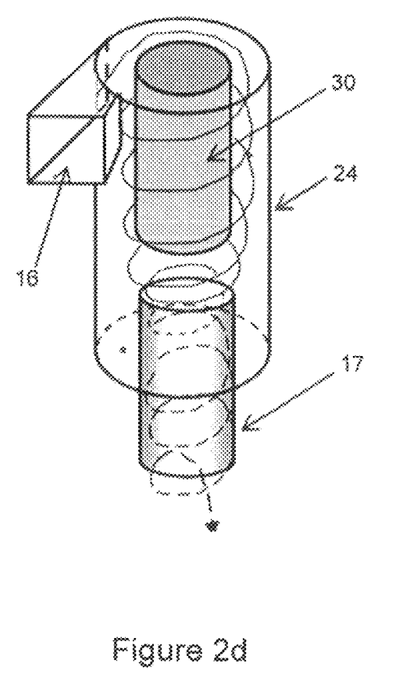
FIG. 2*d* is a schematic perspective view of a PM2.5 sampler showing air flow patterns.
Figure 2E:
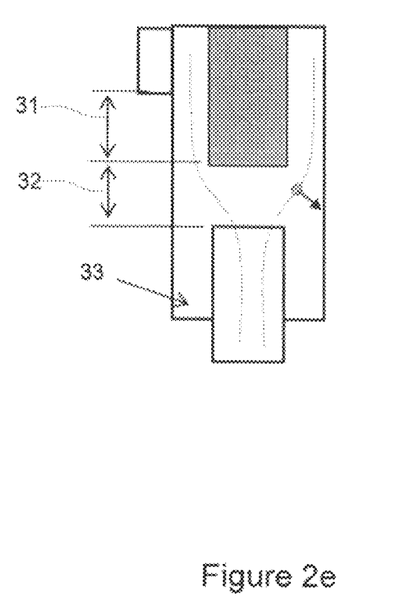
FIG. 2*e* is a schematic side view of the PM2.5 sampler showing air flow patterns.

FIG. 2b shows some of the components within the housing portion 24 of the sampler 12 such as a core portion 30 which is preferably made of a conductive material. As shown in FIG. 2c, the cover portion 28 is integrated with the core portion 30, however, the core portion 30 may be suspended within the housing portion 24 in other ways such as by mounting the core portion 30 to the inside of the housing portion. FIG. 2d is a perspective view of the sampler 12 with a transparent housing 24. As will be understood, the housing portion 24 will typically not be transparent so that the components and operation of the sampler 12 will be hidden from users. A front view of the sampler is shown in FIG. 2e. As can be seen, there is a distance 31 between a bottom of the core portion 30 to a bottom of the inlet port 16. A specified gap 32 is also present between the bottom of the core portion 30 and the top of the outlet port 17 based on the size of the sampler 14. A top portion of the outlet port 17 is preferably manufactured with a sharp inlet angle 34 at about 30 degrees or less, and more preferably less than 15 degrees in order to improve the separation of the particulate matter as schematically shown in FIG. 2c. In other words, the input port or the output port or both, may be isokinetic ports.

In operation, air, more specifically dirty air including various sized particulate matter, is forced into or sucked into the sampler 12 via the inlet port 16. Due to the presence of the core portion 30, the air is forced into a swirling, or cyclone, motion or airflow pattern which creates tangential forces that separate the particulate matter between pieces of particulate matter which are larger than and smaller than the predetermined size of about 2.5 μm. In the disclosure, the air and particulate matter travel and exit in the same direction with the smaller particulate matter exiting through the outlet port and the larger particulate matter passing between the outlet port and the housing port and remaining within the housing portion 24 such as a bunker area 33. As will be understood, there may be larger particulate matter which exits through the outlet port 17 and smaller particulate matter which remains in the bunker area 33, however, it is an accepted factor in PM2.5 sampling or monitoring.

Figure 3:
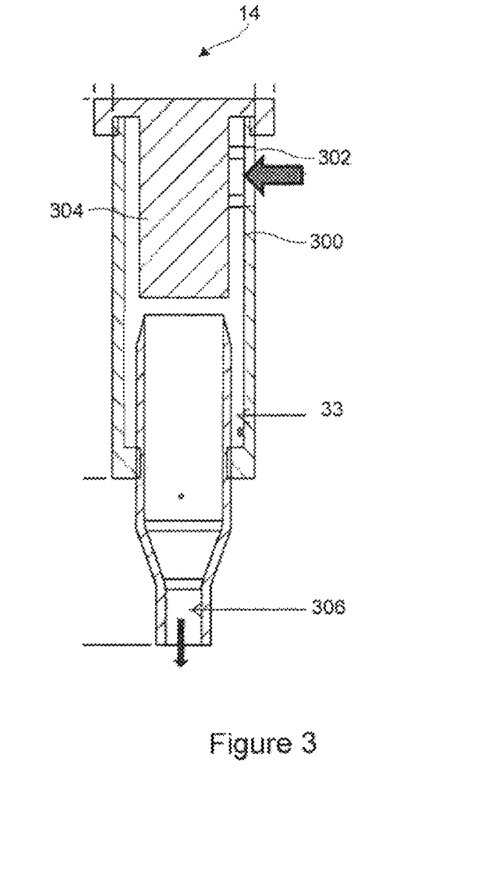
FIG. 3 is a cut-away schematic view of a PM2.5 sampler.

Turning to FIG. 3, a more detailed schematic of the components of another embodiment of a PM2.5 sampler is provided. As shown, the PM2.5 sampler 14 includes a housing portion 300 which includes an inlet port 302 which allows air and particulate matter to enter the housing portion 300. Within the housing portion is a solid core portion 304 at one end of the housing and an outlet port 306 which is located at an opposite end of the housing portion 300. The outlet port 306 may be in threaded connection with the housing portion allowing for easy removal so that the sampler may be cleaned.

As the particulate matter enters the sampler 14 via the inlet port 302, larger particulate matter is separated from the smaller particulate matter while the air rotates around the solid core portion. As described above, larger particulate matter refers to particulate matter which is greater than a predetermined size while smaller particulate matter refers to particulate matter which is less than a predetermined size.

In the current embodiment, the larger particulate matter then settles within the housing portion between the outlet port and the housing portion while the smaller particulate matter travels downstream out of the housing portion via the outlet port.

In a preferred embodiment, the portable 2.5 sampler is designed such that it is portable and is able to mate with an input of a portable particle counter without jeopardizing the efficiency of both particulate collection and separation. Furthermore, although shown as being centrally located within the housing portion, the outlet port may be moved along within the housing portion allowing a user to more easily calibrate the performance of the sampler. Furthermore, in a preferred embodiment, the components (such as the core portion and the outlet port) within the housing portion are removable such that assembly and/or disassembly of the sampler is made easier. This also facilitates the cleaning of components or the inside of the housing portion.

An advantage of the current disclosure is that the sampler is portable which allows for PM2.5 sampling in different locations. There is a desire for users to understand the level of particulate matter in the air at different locations rather than using a permanent fixture at one specific location.

Figure 4:
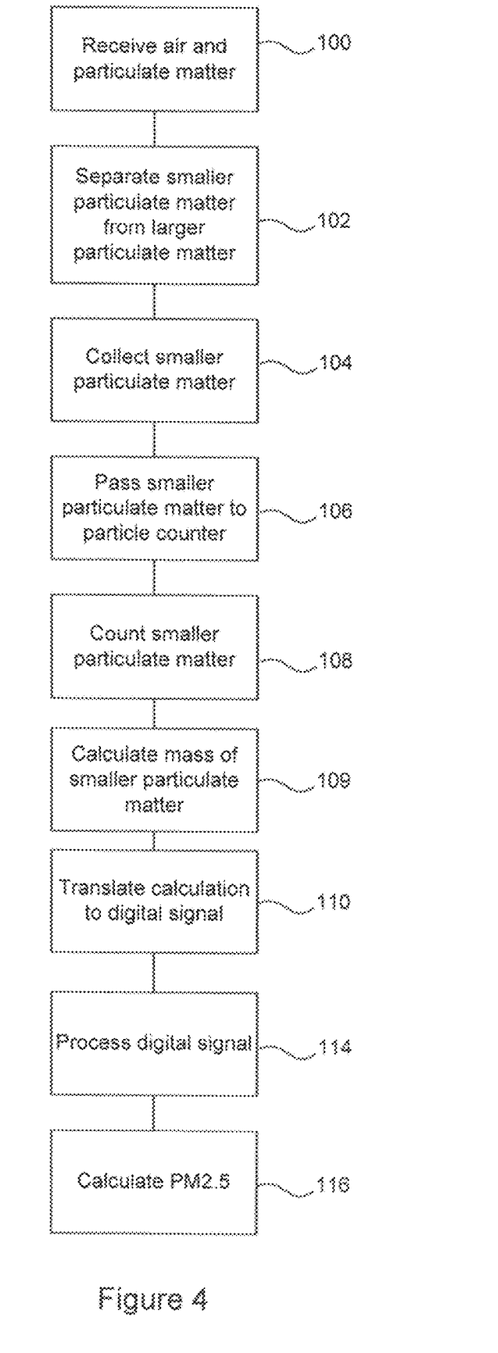
FIG. 4 is a flowchart outlining a method of particulate matter monitoring.

In operation, as schematically shown in FIG. 4, air, containing particulate matter, enters 100 the sampler. The air then passes through the sampler and is forced into a cyclonic flow or airflow pattern which causes the smaller particulate matter to be separate 102 from the larger particulate matter. The smaller particulate matter is then collected 104 and passed 106 through the outlet port to a particle counter which counts 108 the number of particles in the collected smaller particulate matter exiting the sampler 14 and entering the particle counter. A mass of the collected smaller particulate matter, preferably particulate matter smaller than 2.5 µm is then measured of calculated 109. It is understood, and a well expected practice, that some of the collected smaller particulate matter may be larger than the 2.5 µm measurement, however, due to the fact that there would be smaller particulate matter which is collected with the larger particulate matter, the mass of the collected particulate matter can be measured with the assumption that it only contains smaller particulate matter. The measured mass of the smaller particulate matter is then translated 110 into a digital signal representative of the measured mass. The mass determination may be performed by either the particle counter of the central processing unit of by a combination of both. Other characteristics or calculations of the collected smaller particulate matter may also be determined and translated to digital signals to be transmitted and processed by the CPU.

After receiving or determining the digital signals, and more specifically, the digital signal representative of the measured mass, the processor then processes 114 this data to at least calculate the PM2.5 measurement or level 116. This information may then be stored in a database or displayed on a monitor or both.

The above-described embodiments are intended to be examples only. Alterations, modifications and variations can be effected to the particular embodiments by those of skill in the art without departing from the scope, which is defined solely by the claims appended hereto.

What is claimed is:

1. A system for PM2.5 sampling comprising:
   an inlet port for receiving air-borne particulate matter;
   an apparatus for creating a cyclonic airflow pattern within the system to produce a uniflow system to separate larger pieces of particulate matter from smaller pieces of particulate matter, the apparatus being disposed in a housing;
   an outlet port spaced from the inlet port and located below the apparatus for receiving the smaller pieces of particulate matter;
   wherein air flow between the inlet port and the outlet port carries smaller pieces of particulate matter toward a central axis of the cyclonic airflow pattern for reception by the outlet port and the received smaller pieces of particulate matter are transmitted for further counting; and
   wherein a cyclonic air flow circling around the apparatus in a bunker space between the apparatus and the housing and the bunker space retains the larger pieces of particulate matter within the air-borne particulate matter.

2. The system of claim 1, wherein the inlet port is oriented to direct the air flow to enter the inlet port along a tangential direction of the cyclonic airflow pattern.

3. An apparatus for PM2.5 sampling comprising:
   a housing portion for collecting and separating air-borne particulate matter;
   at least one inlet port, connected to the housing portion, for receiving the air-borne particulate matter;
   a core portion, located within the housing portion, the core portion assisting in generating a cyclonic airflow pattern to produce a uniflow system for separating particulate matter below a predetermined size from particulate matter above a predetermined size within the air-borne particulate matter; and
   an outlet port for receiving the particulate matter below the predetermined size, wherein a cyclonic air flow circles around the core portion in a bunker space between the core portion and the housing and the bunker space retains the particulate matter above the predetermined size within the air-borne particulate matter.

4. The apparatus of claim 3 wherein the predetermined size is 2.5 µm in diameter.

5. The apparatus of claim 3 further comprising a cover portion for enclosing the housing portion.

6. The apparatus of claim 5 wherein the cover portion is in a threaded connection with the housing portion.

7. The apparatus of claim 6 wherein the cover portion is integrated with the core portion.

8. The apparatus of claim 3 wherein the inlet port includes a steeped angle wall.

9. The apparatus of claim 8 wherein an angle of the steeped angle wall is less than about 15 degrees.

10. The apparatus of claim 3 wherein the inlet port is located at one end of the housing portion and the outlet port is located at an end of the housing portion opposite the inlet port.

11. The apparatus of claim 3 wherein an inner surface of the housing portion, the inlet port and the outlet port is made from a conductive material.

12. The apparatus of claim 3 wherein the core portion is made from a conductive material.

13. The apparatus of claim 3 wherein the outlet port includes a steeped angle wall.

14. The apparatus of claim 13 wherein an angle of the steeped angle wall is less than about 15 degrees.

15. The system of claim 3, wherein the at least one inlet port is oriented to direct air flow between the inlet port and the outlet port to enter the inlet port along a tangential direction of the cyclonic airflow pattern to create the cyclonic air flow for particulate matter separation.

16. The system of claim 15, wherein the air flow between the inlet port and the outlet port enters the outlet port substantially along a central axial direction of the cyclonic airflow pattern.

17. The system of claim 15, wherein the outlet port is spaced from and located below the core portion and wherein the particulate matter below the predetermined size within the air-borne particulate matter is carried by the cyclonic air flow toward a central axis of the cyclonic airflow pattern before entering the outlet port.

18. The system of claim 3, wherein the core portion is located above and spaced form the outlet port at a gap distance.

19. The system of claim 18, wherein the gap distance is adjustable.

20. The system of claim 19, wherein the outlet port is in a threaded connection with the housing portion and is movable along a longitudinal direction of the housing to adjust the gap distance.

21. An apparatus for portable PM2.5 monitoring comprising:
- a PM2.5 sampling device including:
  - a housing portion for collecting and separating air-borne particulate matter,
  - an inlet port, connected to the housing portion, for receiving the air-borne particulate matter,
  - a core portion, located within the housing portion, the core portion assisting in generating a cyclonic airflow pattern to produce a uniflow system for separating particulate matter below a predetermined size from particulate matter above a predetermined size within the air-borne particulate matter, and
  - an outlet port for receiving the particulate matter below the predetermined size;
- a particle counter, connected to the outlet port, for receiving the particulate matter smaller than the predetermined size and for determining a mass of the particulate matter below the predetermined size; and
- a processor for determining a PM2.5 level based on the mass of the particulate matter below the predetermined size,
- wherein a cyclonic air flow circles around the core portion in a bunker space between the core portion and the housing and the bunker space retains the particulate matter above the predetermined size within the air-borne particulate matter.

22. The system of claim 21, wherein the inlet port is oriented to direct air flow carrying the air-borne particulate matter to enter the inlet port along a tangential direction of the cyclonic airflow pattern.

* * * * *